United States Patent [19]

Guzik et al.

[11] 4,424,393

[45] Jan. 3, 1984

[54] PROCESS OF PREPARATION OF SUBSTITUTED DIPHENYL ETHERS

[75] Inventors: Frederick F. Guzik, Wadsworth; Steven E. Pamer, Rittman; Sidney B. Richter, Fairlawn, all of Ohio

[73] Assignee: PPG Industries, Inc., Pittsburgh, Pa.

[21] Appl. No.: 295,885

[22] Filed: Aug. 24, 1981

[51] Int. Cl.$^3$ .................................................. C07C 79/46
[52] U.S. Cl. .................................. 560/21; 260/455 R; 260/465 D; 260/544 N; 260/544 D; 568/656; 568/655
[58] Field of Search ....................... 260/465 D, 455 R; 560/21

[56] References Cited

U.S. PATENT DOCUMENTS

| | | | |
|---|---|---|---|
| 2,813,128 | 11/1957 | Anthony | 260/612 |
| 3,758,622 | 9/1973 | Watson et al. | 260/668 R |
| 3,798,276 | 3/1974 | Bayer et al. | 560/21 |
| 3,928,416 | 12/1975 | Bayer et al. | 560/21 |
| 3,950,379 | 4/1976 | Bayer | 560/21 |
| 3,979,437 | 9/1976 | Theissen | 560/21 |
| 4,039,588 | 8/1977 | Wilson et al. | 560/21 |
| 4,165,337 | 8/1979 | Yoshinaka et al. | 260/544 D |
| 4,323,692 | 4/1982 | Tanger | 560/65 |

*Primary Examiner*—Paul J. Killos
*Attorney, Agent, or Firm*—Edward J. Whitfield

[57] ABSTRACT

This invention relates to a process for preparing herbicidally active substituted diphenylethers. Also, this invention provides novel intermediates useful in the production of said diphenylethers.

4 Claims, No Drawings

PROCESS OF PREPARATION OF SUBSTITUTED DIPHENYL ETHERS

DESCRIPTION OF THE INVENTION

This invention concerns preparing substituted herbicidally active diphenyl ethers represented by the formula:

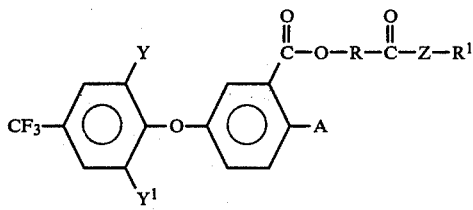

wherein:
- A is nitro, halogen or cyano
- Y is hydrogen or halogen;
- $Y^1$ is hydrogen, halogen, cyano, trifluoromethyl or alkyl containing 1 to 4 carbon atoms;
- Z is oxygen or sulfur;
- R is alkylene containing 1 to 3 carbon atoms which may be monosubstituted by a substituent selected from alkyl, oxoalkyl or hydroxyalkyl containing 1 to 4 carbon atoms; and
- $R^1$ is hydrogen, alkyl or alkoxy containing 1 to 10 carbon atoms, cycloalkyl containing 3 to 8 carbon atoms, an agronomically acceptable ionic species or

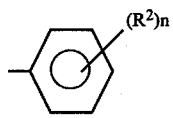

wherein $R^2$ is selected from halogen, alkyl or alkoxy containing 1 to 10 carbon atoms, cyano, nitro, or trifluoromethyl and n is 0, 1, 2, or 3.

Exemplary of halogens represented in the above formula are, for example, bromine, chlorine, iodine, or fluorine, preferably bromine or chlorine. Some alkyl and cycloalkyl groups represented in the above formula are, for example, methyl, ethyl, n-propyl, isopropyl, isobutyl, n-butyl, t-butyl, n-amyl, heptyl, octyl, isooctyl, nonyl, decyl, cyclopropyl, cyclopentyl, cyclohexyl, cyclooctyl, and the like. Suitable alkoxy, oxoalkyl and hydroxyalkyl groups are, for example, methoxy, ethoxy, butoxy, octoxy, oxoethyl, oxopropyl, oxobutyl, hydroxymethyl, hydroxyethyl, hydroxypropyl, hydroxybutyl, and the like. Methylene, ethylene, or n-propylene are exemplary of suitable alkylene groups. As examples of agronomically acceptable ionic species, there may be mentioned alkali metals such as sodium, potassium, or lithium; alkaline earth metals such as barium or calcium; ammonium; or alkylammonium or alkanolammonium containing 1 to 4 carbon atoms.

Preferred compounds prepared by the process of this invention are those wherein Z is oxygen, A is nitro or halogen, e.g. bromine; R is methylene substituted by a methyl group, i.e. an ethylidene group; $R^1$ is alkyl of up to 4 carbon atoms, e.g., an ethyl group; Y is hydrogen, and $Y^1$ is halogen, e.g. chlorine.

Compounds of the above formula (I) are fully described in copending, commonly assigned application Ser. No. 163,460, filed June 27, 1980. Some specific examples of compounds within the scope of said formula (I) and which may be prepared in accordance with this invention are 1'-(ethoxycarbonyl)ethyl 5-(2-chloro-4-trifluoromethylphenoxy)-2-nitrobenzoate; 1'-(ethoxycarbonyl) 2-propyl 5-(2-chloro-4-trifluoromethylphenoxy)-2-nitrobenzoate; 2'-carboxyethyl 5-(2-chloro-4-trifluoromethylphenoxy)-2-nitrobenzoate; 2'-(ethoxycarbonyl)ethyl 5-(2-chloro-4-trifluoromethylphenoxy)-2-nitrobenzoate; 1'-(ethoxycarbonyl)methyl 5-(2-chloro-4-trifluoromethylphenoxy)-2-nitrobenzoate; 1'-ethoxycarbonyl-2-oxopropyl 5-(2-chloro-4-trifluoromethylphenoxy)-2-nitrobenzoate; 1'-(ethoxycarbonyl)butyl 5-(2-chloro-4-trifluoromethylphenoxy)-2-nitrobenzoate; 1'-(phenoxycarbonyl)ethyl 5-(2-chloro-4-trifluoromethylphenoxy)-2-nitrobenzoate; 1'-(ethoxycarbonyl)propyl 5-(2-chloro-4-trifluoromethylphenoxy)-2-nitrobenzoate; 1'-ethoxycarbonyl-3'-methylbutyl 5-(2-chloro-4-trifluoromethylphenoxy)-2-nitrobenzoate; 1'-(ethoxycarbonyl)ethyl 5-(2-chloro-4-trifluoromethylphenoxy)-2-bromobenzoate; 1'-(ethoxycarbonyl)-2'-hydroxypropyl 5-(2-chloro-4-trifluoromethylphenoxy)-2-nitrobenzoate; 1'-(ethoxycarbonyl)ethyl 5-(2-chloro-4-trifluoromethylphenoxy)-2-cyanobenzoate; 1'-(ethoxycarbonyl)ethyl 5-(2,6-dichloro-4-trifluoromethylphenoxy)-2-nitrobenzoate; 1'-(ethoxycarbonyl) ethyl 5-(2-chloro-6-bromo-4-trifluoromethylphenoxy)-2-cyanobenzoate; and 1'-(thioethylcarbonyl)ethyl 5-(2-chloro-4-trifluoromethylphenoxy)-2-nitrobenzoate.

It is, of course, to be further understood that the preparation of stereo and optical isomers of compounds represented by the above formula (I) are within the scope of this invention.

A compound of formula (I) is prepared, in accordance with this invention by a multi-stage reaction, which in the first stage involves halogenating, in the presence of a free radical initiator, 3-(2- and/or 6-substituted-4-trifluoromethylphenoxy)-m-toluene to the corresponding 3-(2- and/or 6-substituted-4-trifluoromethylphenoxy) benzotrihalide according to the following exemplary photochlorination reaction:

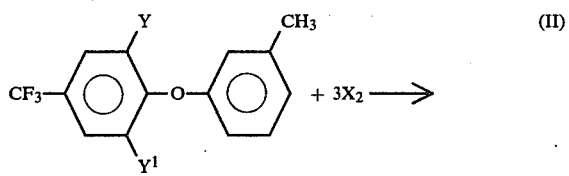

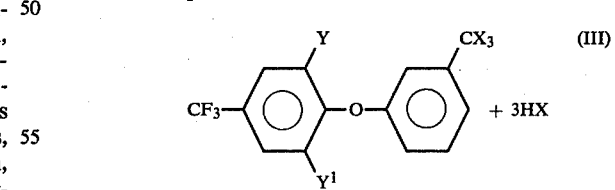

wherein Y and $Y^1$ in the above formulae (II) and (III) are as defined with respect to formula (I) and X is halogen, e.g. chlorine or bromine, preferably chlorine.

Although in the above described reaction, free radical halogenation is preferably initiated by ultraviolet radiation, any free radical initiator that generates free radicals at the halogenation temperature, e.g. organic azo or peroxy compounds, may be used. The amount of initiator used is not critical so long as a threshold level of free radicals are provided to initiate and maintain the halogenation reaction. Such amount is typically referred to as an initiating amount.

Any source of light that will provide the necessary useful radiation can be used. Such radiation is generally available at wavelengths in the near ultraviolet. Thus a common household tungsten filament light bulb, sun lamp, mercury arc lamp, or sunlight itself, can be used as a source of ultraviolet light. The quantum of radiation required is difficult of precise definition; however, one skilled in the art can readily ascertain whether quantum of useful radiation is adequate for the quantity of reactants used by observing whether the halogenation reaction occurs. The light source for the photohalogenation may, of course, be located within the particular reactor or externally of the reactor, in which latter case means must be provided for radiation to enter the reactor, e.g. by use of a glass reactor or a glass sight port.

As beforesaid, in addition to photo initiation, the halogenation reaction can be initiated by an organic free radical initiator, e.g. organic azo or peroxy compound, including dialkyl peroxydicarbonates, peroxy esters and the like. The particular free radical initiator used is not critical provided it is compatible with the reactants and any solvent system used, i.e., it is chemically nonreactive and efficiently generates free radicals at the halogenation temperature selected. In addition, the free radical initiator should be substantially anhydrous and substantially free of materials such as solvents, oils or the like that are capable of halogenation.

One skilled in the art can readily select an appropriate initiator with the help of published half-life data, which is a means of expressing the rate of decomposition of the initiator at a particular temperature. Some specific examples of commonly employed free-radical initiating compounds include diacyl peroxides such as acetyl peroxide, benzoyl peroxide, caprylyl peroxide, p-chlorobenzyl peroxide, 2,4-dichlorobenzoyl peroxide, lauroyl peroxide or propionyl peroxide; peroxyesters such as t-butyl peroxyacetate, t-butyl peroxy(2-ethyl-hexanoate), t-butyl peroxyisobutyrate or t-butyl peroxypivalate; dialkyl peroxydicarbonates such as diethyl, diisopropyl, di-n-propyl, disecbutyl, diisobutyl, di-n-butyl, di-t-butyl, dicapryl, diethylhexyl, dicyclohexyl or di-4-t-butyl cyclohexyl peroxydicarbonate; mono peroxydicarbonates such as t-butylperoxy isopropylcarbonate; and azo compounds such as azo-bis-isobutyronitrile.

As in the case of ultraviolet radiation, only that amount of organic free radical initiator that is required to initiate and maintain the halogenation reaction need be used, i.e., an initiating amount, which amount can be readily determined by one skilled in the art, depending on the halogenation temperature and the quantity of reactants. The organic free radical initiator would, of course, be introduced into the halogenation reactor continuously for a continuous halogenation, as distinguished from a batch halogenation so as to maintain a continuous supply of free radicals in the reaction medium.

As regards the reaction medium, the halogenation reaction may, if desired, be conducted in an inert organic solvent liquid, use of which assists in controlling reaction temperature. The organic liquid or solvent should be chemically inert to the reactants and reaction products and preferably is one in which the reaction products are soluble. As examples of such solvents, there may be mentioned carbon tetrachloride, chlorofluorinated oils or polychlorinated aromatics such as 1,2,4-trichlorobenzene. Also contemplated are liquid polyhalogenated aliphatic hydrocarbons containing from 1 to 4 carbon atoms such as methylene chloride, ethylene dichloride, chloroform, trichloroethylene or perchloroethylene. Carbon tetrachloride is a particularly useful solvent since it is chemically inert and is a solvent for both the reactants and reaction products.

The particular organic solvent and the amount thereof are not particularly critical. Only that amount of organic solvent is needed to solubilize the reactants and reaction products, form a workable liquid reaction medium and serve as a heat sink for the heat of reaction. The quantity of organic solvent may vary over a wide range, but typically the weight ratio of organic liquid to formula (II) compound is from about 1:1 to about 10:1.

Typically, stoichiometric amounts of halogen to formula (II) compound are employed, but to assure complete halogenation of the methyl group to the trihalomethyl group, up to about a ten percent excess of halogen may be used. The temperature at which the halogenation reaction is conducted may also vary, e.g. between about 20° C. and about 100° C. Typically, the reaction will be conducted between about 40° C. and about 90° C., and preferably between about 60° C. and 80° C.

The temperature at which the halogenation reaction is conducted will also depend on the nature of the organic liquid reaction solvent. At, for example, atmospheric pressure, the maximum reaction temperature will be determined by the boiling point of the organic liquid solvent or in the absence of solvent, the temperature at which the reaction mixture boils. Obviously, if the reaction temperature is above the boiling point of the reacting mixture, the reaction is conducted at a pressure sufficiently above atmospheric to maintain the reacting mixture in the liquid phase. The halogenation reaction is conveniently conducted at atmospheric or ambient pressure; however, when operated continuously pressures above atmospheric are used to overcome the pressure drop in equipment and piping downstream of the reactor. Of course, the reaction can be conducted at reduced, i.e. less than atmospheric pressure, if, for example, a lower operating temperature is desired.

As to the halogen source, although it is preferred to use elemental chlorine or bromine other chlorinating or brominating agents may also be used, some examples of which are phosphorous trichloride, phosphorous pentachloride, phosphorous oxychloride, hydrogen chloride, phosgene, thionyl chloride, sulfuryl chloride, hypochlorite compounds, or hydrogen bromide. If desired, the halogenation reaction may be conducted in the presence of a catalyst such as disclosed in U.S. Pat. No. 3,547,960. The amount of catalyst used is of course that amount which is required to accelerate the reaction to a commercially acceptable rate. Exemplary of commonly used halgenation catalysts are imidazole or N,N-dimethylformamide. In addition, the halogenation reaction may be conducted in the presence of an acid acceptor, for example, pyridine.

In the second stage of the process of this invention for preparing a compound of formula (I), the formula (III) compound (which itself is believed to be novel) prepared by free radical halogenation of a formula (II) compound, is converted to the corresponding 3-(2- and/or -6-substituted-4-trifluoromethylphenoxy) benzoic acid by hydrolysis in the presence of aqueous acetic acid as follows:

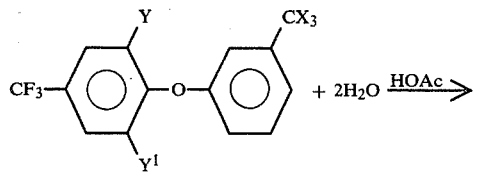

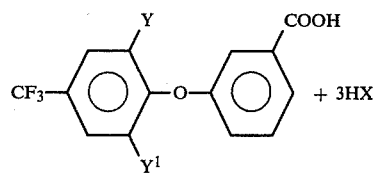

The above hydrolysis is conducted in conventional fashion under typical hydrolysis conditions. Although the hydrolysis reaction proceeds in the absence of catalyst, reaction time may be considerably reduced by conducting the reaction in the presence of a catalytic amount of a Lewis acid or Friedel-Crafts catalyst, e.g. ferric chloride.

In the third stage of the process according to this invention, the formula (IV) compound is converted to the acid salt form by reaction with an alkali metal base as follows:

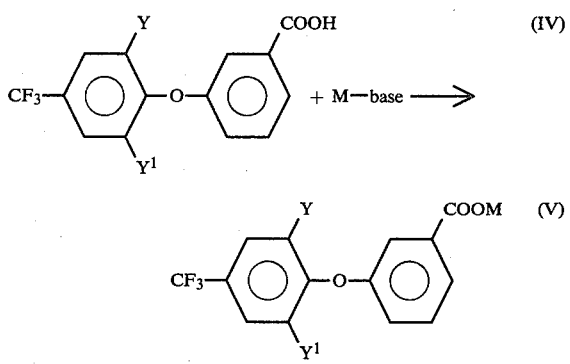

when M is an alkali metal, such as sodium, potassium or lithium. In the above reaction any alkali metal base may be used such as sodium hydroxide, potassium hydroxide, lithium hydroxide, sodium carbonate, potassium carbonate or lithium carbonate. Preferably sodium hydroxide or potassium hydroxide are used to form the acid salt of formula (V). Conversion of the formula (IV) compound to the salt form is typically conducted in a polar organic solvent such as $C_1$ to $C_4$ saturated aliphatic alcohol, dimethylsulfoxide or dimethylformamide at a temperature in the range of from about 50° C. to about 200° C. Preferred solvents are the $C_1$ to $C_4$ aliphatic alcohols, such as methanol, ethanol, isopropanol or t-butanol, methanol being preferred. When using an alcohol solvent, the formula (V) compound is isolated by distillation. Alternatively the formula (V) compound can be prepared using aqueous base, e.g. 50 percent aqueous potassium hydroxide solution. In this latter case, the formula (V) compound may be isolated by adding polar aprotic solvent together with an organic solvent such as toluene or benzene. Some or all of the water may be removed by conventional azeotropic distillation.

In the fourth stage of the process according to this invention, the formula (V) compound is reacted with an α-halocarboxylic acid ester or thio ester to form the corresponding diester as follows:

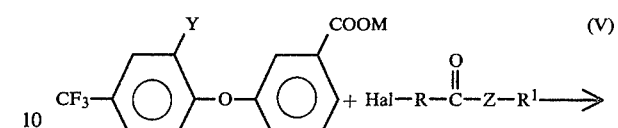

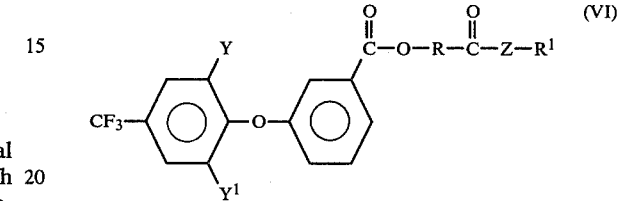

wherein R, $R^1$, and Z are defined with reference to the formula (I) compound and Hal is halogen, preferably bromine or chlorine. The above esterification reaction is conducted in the liquid phase at a temperature usually in the range of from about 50° C. to about 200° C. and typically in the presence of polar aprotic solvent. Although stoichiometric amounts of formula (V) compound and α-halocarboxylic acid ester may be used, to assure complete reaction a slight excess, i.e. up to about 5 percent, of the α-halocarboxylic acid ester is typically advantageously employed.

In the fifth and final stage of the process of this invention the formula VI compound is converted to the formula (I) compound by introduction of a nitro, a halogen or a cyano functionality ortho to the diester grouping. If, for example, it is desired to prepare a nitrated formula (I) compound, the formula (VI) compound may be reacted with any conventional nitrating agent, e.g. nitric acid, as follows:

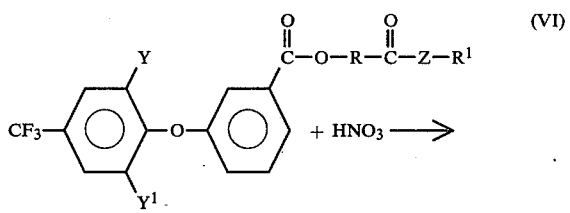

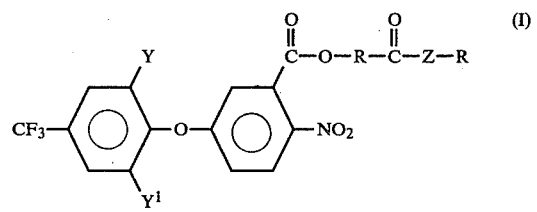

In addition to nitric acid, other nitrating agents may be used, e.g. mixed acids such as nitric acid/sulfuric acid, potassium nitrate/sulfuric acid or nitric acid/sulfuric acid/acetic anhydride, the latter being preferably used. The nitration is typically conducted at a temperature in the range of from about 0° C. to about 70° C. and usually in the range of from about 20° C. to about 50° C. The nitration is usually conducted under substantially anhydrous conditions in an inert, e.g. nitrogen, atmosphere. Although stoichiometric amounts of formula (VI) compound and nitrating agent may be employed, the latter is typically employed in excess and usually from about 10 to 50 percent molar excess. The nitration may if desired be conducted in the presence of an inert solvent such as, for example, diethylether, cyclohexane, hexane, heptane, methylene chloride, ethylene dichloride, chloroform, carbon tetrachloride, trichloroethylene, perchloroethylene, benzene, toluene, monochlorobenzene, dichlorobenzene or the like.

If it is desired to introduce a halogen or cyano functionality in the formula (I) compound, the formula (VI) compound is accordingly treated using conventional halogenation or cyanation techniques.

Although as described herein, introduction of the nitro, halogen or cyano functionalities is preferably performed as the final step of the reaction sequence, this invention in its broadest aspect contemplates introduction of these functionalities at any stage of the reaction sequence and also includes using as a starting material a nitrated, halogenated or cyanated compound corresponding to the formula (II) compound. Furthermore, this invention contemplates preparation of a compound of the formula (III) both per se, and in its nitrated, halogenated or cyanated form, which compound is believed novel and useful as a valuable intermediate in the preparation of a compound of formula (I) as well as other substituted diphenyl ether herbicides, e.g. those described in U.S. Pat. Nos. 3,928,416 and 4,063,929 and published European Patent Application No. 23100.

This invention also contemplates hydrolysis of a formula (III) compound in similar fashion to that previously described except that equimolar amounts of water and formula (III) compound are used to convert the latter to the corresponding 3-(2- and/or 6-substituted-4-trifluromethylphenoxy) benzoyl halide as follows:

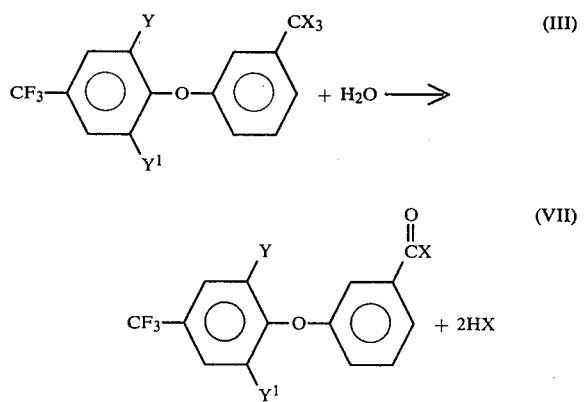

The benzoyl halides of formula (VII) are also valuable intermediates that may also be used to prepare a compound of formula (I) as well as other substituted diphenyl ether herbicides. For example, the formula (VII) compound may be reacted with an α-hydroxy carboxylic acid ester or thioester to form a compound of formula (VI), as follows:

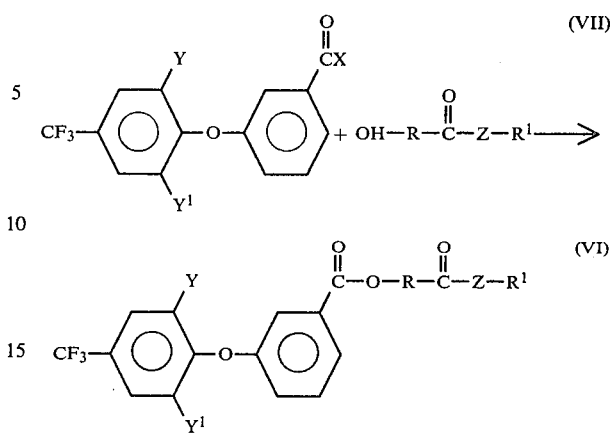

The formula (VI) compound is then treated as described previously depending on whether a 2-nitro, a 2-halo or a 2-cyano compound of formula (I) is desired.

The invention is further illustrated by the following examples which describe the preparation of preferred substituted diphenyl ethers of this invention.

EXAMPLE 1

PREPARATION OF 3-(2-CHLORO-4-TRIFLUOROMETHYL-PHENOXY) BENZOTRICHLORIDE

The reactor used comprised a 1000-milliliter capacity, 3-necked cylindrical pyrex glass vessel approximately 9 centimeters in diameter by 24 centimeters in height. Through the center neck of the reactor was positioned a quartz immersion well which housed the source of ultra violet radiation, namely a 200-watt Hanovia No. 654 A-36 mercury vapor lamp emitting light over the spectral range of from 2,200 to 14,000 Å. The quartz immersion well was jacketed for circulation of cooling water. The reactor was further provided with a magnetic stirring bar, thermometer and a Claisen adapter to which was fitted a water condenser topped with a dry ice/acetone Dewar condenser. A dip tube having a medium porosity fritted tip extended to within two inches from the bottom of the reactor. The reactor was further wrapped with heating tape and positioned on a combination hot plate/stirrer. The reactor was, in addition, shielded by wrapping in a thick layer of aluminum foil and was also vented to a caustic scrubber.

The reactor was charged with 89.6 grams (0.30 mole) of 3-(2-chloro-4-trifluoromethylphenoxy) toluene (a compound of formula II), 0.6 gram of hexamethylenetetramine and 600 milliliters of carbon tetrachloride. The reactor contents were then heated to about 65° C. and gaseous chlorine was bubbled in at a rate of about 0.6 gram per minute. The reaction mixture was periodically sampled to determine completeness of reaction. After 4 hours, heating and chlorine addition were discontinued and the reaction mixture was stirred overnight. The reaction mixture was then concentrated on a rotary evaporator at 75° C. and 0.5 mm Hg pressure leaving 126.5 grams of a thick yellow liquid, which, upon standing solidified into a thick crystalline mass. The crystalline mass was broken-up, washed with 60 milliliters of n-hexane, and suction filtered affording 92 grams of fine, white crystals melting between 85° C. and 89° C. and identified as 3-(2-chloro-4-trifluoromethylphenoxy) benzotrichloride (a compound of formula III).

EXAMPLE 2

PREPARATION OF 5-(2-CHLORO-4-TRIFLUOROMETHYLPHENOXY)-2-NITROBENZOTRICHLORIDE

To a 100 milliliter, 3-necked flask provided with an addition funnel, a magnetic stirring bar and a drying tube was charged 7.48 grams (0.02 mole) of 3-(2-chloro-4-trifluoromethylphenoxy) benzotrichloride (prepared as described in Example 1) in 10 milliliters of methylene chloride. To this stirred solution, cooled in an ice bath, was added 6.12 grams (0.06 mole) of acetic anhydride and 0.5 milliliter (0.92 gram) of concentrated sulfuric acid. When the mixture cooled to 5° C., concentrated nitric acid was added dropwise at a rate such that the temperature of the reaction mixture did not rise above 10° C. A total of 1.3 milliliters (0.02) mole of concentrated nitric acid was added over a 9 minute period. After stirring for 90 minutes at a temperature between 5° C. and 10° C., the reaction mixture was poured into 200 milliliters of ice/water, phase separated and the aqueous layer extracted with methylene chloride. The methylene chloride extract was combined with the organic phase, washed with water and saturated aqueous sodium chloride solution and dried over anhydrous magnesium sulfate. Filtration and evaporation of solvent afforded 8.07 grams of a viscous yellow oil, identified as 5-(2-chloro-4-trifluoromethylphenoxy)-2-nitrobenzotrichloride.

EXAMPLE 3

PREPARATION OF 1'-(ETHOXYCARBONYL)ETHYL 5-(2-CHLORO-4-TRIFLUOROMETHYLPHENOXY)-2-NITROBENZOATE (a) To a 100 milliliter, 3-necked flask provided with a magnetic stirring bar, a reflux condenser and a thermometer was charged 19.5 grams (0.05 mole) of 3-(2-chloro-4-trifluoromethylphenoxy) benzotrichloride (prepared as described in Example 1), 25 milliliters of glacial acetic acid, 0.2 grams of ferric chloride hexahydrate and 1.8 grams (0.1 mole) of water. The reaction mixture was heated to reflux and maintained at reflux for six hours. After reflux was discontinued, an additional 25 milliliters of water was added, with stirring to the warm solution, resulting in the formation of a thick off-white precipitate which was suction filtered and dried to constant weight affording 15.3 grams of material melting at 123° C. to 125° C. and identified as 3-(2-chloro-4-trifluoromethylphenoxy) benzoic acid (a compound of formula IV).

(b) To a one-liter, 3-necked flask provided with a thermometer, distillation column, and a power-driven stirrer was charged 29.4 grams (0.525 mole) of a solution of anhydrous potassium hydroxide in 350 milliliters of methanol. To this solution, maintained at a temperature of 50° C., was added 157.7 grams of 3-(2-chloro-4-trifluoromethylphenoxy) benzoic acid (prepared as described in paragraph (a) of this Example) in 250 milliliters of methanol. The reaction mixture was then heated to distillation temperature and distilled until about 530 milliliters of methanol was collected, after which about 150 milliliters of toluene was added and distillation continued until substantially all of the water was removed azeotropically. After cooling to about 50° C., 200 milliliters of dimethylsulfoxide and 68.25 grams (0.5 mole) of ethyl 2-chloropropionate was added. The reaction mixture was then heated to 110° C. and maintained at 110° C. for 16 hours. The reaction mixture was then cooled, poured into 500 milliliters of water and extracted with 200 milliliters of methylene chloride. The organic layer was then washed with five 250 milliliter portions of water, stripped in a rotary evaporator and dried over anhydrous magnesium sulfate affording 124.9 grams of product, identified as 1'-(ethoxycarbonyl)ethyl 3-(2-chloro-4-trifluoromethylphenoxy) benzoate (a compound of formula VI).

(c) To a 5-liter, 4-necked flask provided with a thermometer, reflux condenser, and a power-driven stirrer was added, under a nitrogen blanket, 1,130 grams (2.71 moles) of 1'-(ethoxycarbonyl)ethyl 3-(2-chloro-4-trifluoromethylphenoxy) benzoate (prepared as described in paragraph (b) of this Example), 1,500 milliliters of methylene chloride, 768 milliliters (8.13 moles) of acetic anhydride and 851 milliliters of concentrated sulfuric acid. To this reaction mixture, maintained via an ice bath at 20° C. to 25° C. was added 174 milliliters (2.71 moles) of concentrated nitric acid over a one hour period. Subsequently, an additional 307 milliliters (3.75 moles) of acetic anhydride and 70 milliliters (1.08 moles) of nitric acid were added and the reaction mixture was stirred overnight at ambient temperature. The reaction mixture was then poured into 15 liters of water, phase separated and the organic phase was washed with 2 liters of 4 percent aqueous sodium hydroxide solution and 2 liters of 6 percent aqueous ammonium hydroxide solution. (To assist phase separation, a sufficient quantity of saturated aqueous sodium chloride solution was also added.) After phase separation, the organic phase was washed with water, filtered, topped on a rotary evaporator at 75° C. and dried over anhydrous magnesium sulfate affording 1,115 grams of viscous liquid identified as 1'-(ethoxycarbonyl)ethyl 5-(2-chloro-4-trifluoromethylphenoxy)-2-nitrobenzoate (a compound of formula I).

EXAMPLE 4

PREPARATION OF 3-(2-CHLORO-4-TRIFLUOROMETHYLPHENOXY) BENZOYL CHLORIDE

To a 100 milliliter, 3-necked flask provided with a magnetic stirring bar, a thermometer, an addition funnel and a venting tube was charged 39 grams (0.10 mole) of 3-(2-chloro-4-trifluoromethylphenoxy) benzotrichloride (prepared as described in Example 1), and 0.12 grams of anhydrous ferric chloride. The mixture was heated to 110° C. and 1.8 grams (0.1 mole) of water was added dropwise over a 20 minute period. After heating for an additional hour at 110° C., the mixture was cooled and taken up in 50 milliliters of methylene chloride. The mixture was treated with powdered charcoal, filtered through a bed of Celite ® and topped on a rotary evaporator at 75° C., affording 31 grams of material identified as 3-(2-chloro-4-trifluoromethylphenoxy) benzoyl chloride (a compound of formula VII).

While the preparation of preferred compounds of the invention have been described in some detail by the foregoing examples, it will be understood that any compound within the scope of this invention may be prepared by one skilled in the art simply by varying the choice of starting materials. Moreover, although the invention has been described with reference to specific details of certain illustrative embodiments, it is not intended that it be so limited, except insofar as such details appear in the appended claims.

We claim:

1. A process for preparing a compound of the formula:

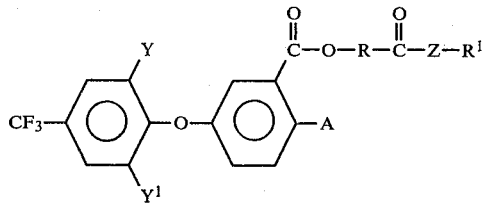

wherein:
A is nitro,
Y is hydrogen or halogen;
Y¹ is hydrogen, halogen, cyano, trifluoromethyl or alkyl containing 1 to 4 carbon atoms;
Z is oxygen or sulfur;
R is alkylene containing 1 to 3 carbon atoms which may be monosubstituted by a substituent selected from alkyl, oxoalkyl or hydroxyalkyl containing 1 to 4 carbon atoms; and
R¹ is hydrogen, alkyl or alkoxy containing 1 to 10 carbon atoms, cycloalkyl containing 3 to 8 carbon atoms, an agromonically acceptable ionic species or

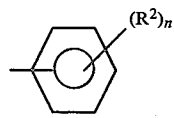

wherein R² is selected from halogen, alkyl or alkoxy containing 1 to 10 carbon atoms, cyano, nitro, or trifluoromethyl and n is 0, 1, 2, or 3;
by the steps of:
(a) halogenating in an inert organic liquid reaction medium, at a temperature of from 20° C. to 100° C., and in the presence of a free radical initiator a 3-(2- and-/or 6-substituted-4-trifluoromethylphenoxy)-m-toluene compound of the formula:

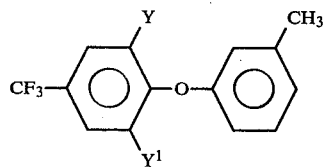

to form the corresponding 3-(2- and/or 6-substituted-4-trifluoromethylphenoxy) benzotrihalide;
(b) hydrolyzing the benzotrihalide of step (a) in the liquid phase with aqueous acetic acid to prepare a substituted benzoic acid compound of the formula:

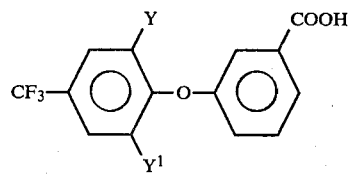

(c) reacting the substituted benzoic acid of step (b) with an alkali metal base, in a polar organic solvent, at a temperature from 50° C. to 200° C., to form the corresponding acid salt;
(d) reacting the acid salt formed in step (c) with an γ-halocarboxylic acid ester of the formula:

Hal—R—COZ—R¹ wherein Hal is halogen, in a polar organic solvent and a temperature of from 50° C. to 200° C., to form a compound of the formula:

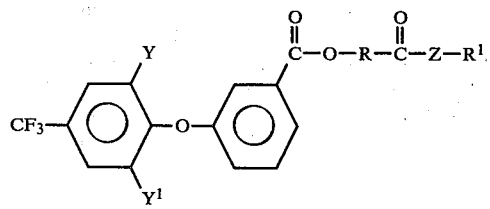

(e) converting the compound prepared in step (d) to the corresponding 2-nitro derivative by nitration, at a temperature from 0° C. to 70° C., with a nitrating agent selected from nitric acid, nitric acid/sulfuric acid, potassium nitrate/sulfuric acid, or nitric acid/sulfuric acid/acetic anhydride.

2. The process of claim 1, wherein the compound defined in step (a) is chlorinated in the presence of a free-radical initiator.

3. The process of claim 2 wherein the chlorination step is effected by reaction of a compound defined in step (a) with gaseous chlorine in the presense of a free radical initiating quantum of ultra violet radiation.

4. The process of claim 1 wherein the compound 1'-(ethoxycarbonyl)ethyl, 5-(2-chloro-4-trifluoromethylphenoxy)-2-nitrobenzoate is prepared by the steps of:
(a) chlorinating 3-(2-chloro-4-trifluoromethylphenoxy)m-toluene to 3-(2-chloro-4-trifluoromethylphenoxy)benzotrichloride;
(b) hydrolyzing 3-(2-chloro-4-trifluoromethylphenoxy) benzotrichloride to 3-(2-chloro-4-trifluoromethylphenoxy)benzoic acid;
(c) converting 3-(2-chloro-4-trifluoromethylphenoxy) benzoic acid to the corresponding alkali metal salt;
(d) reacting 3-(2-chloro-4-trifluoromethylphenoxy) benzoic acid alkali metal salt with 2-chloropropionate to form 1'-(ethoxycarbonyl) ethyl 3-(2-chloro-4-trifluoromethylphenoxy) benzoate; and
(e) nitrating 3-(2-chloro-4-trifluoromethylphenoxy) benzoate.

* * * * *